United States Patent [19]

Podder et al.

[11] Patent Number: 4,771,067

[45] Date of Patent: Sep. 13, 1988

[54] PROCESS FOR THE PRODUCTION OF 4-NITRODIPHENYLAMINES

[75] Inventors: Chiraranjan Podder, Dormagen; Harro Schlesmann, Odenthal, both of Fed. Rep. of Germany

[73] Assignee: Bayer Aktiengesellschaft, Leverkusen, Fed. Rep. of Germany

[21] Appl. No.: 90,430

[22] Filed: Aug. 26, 1987

Related U.S. Application Data

[63] Continuation of Ser. No. 862,608, May 12, 1986, abandoned.

[30] Foreign Application Priority Data

May 22, 1985 [DE] Fed. Rep. of Germany ....... 3518272

[51] Int. Cl.$^4$ .............................................. C07C 85/04
[52] U.S. Cl. .................................................. 564/406
[58] Field of Search ........................................ 564/406

[56] References Cited

U.S. PATENT DOCUMENTS

| | | | |
|---|---|---|---|
| 1,994,845 | 3/1935 | Wuontz | 564/406 |
| 2,927,943 | 3/1960 | Merz | 564/406 |
| 3,055,940 | 9/1962 | Merz | 564/406 |
| 3,121,736 | 2/1964 | Lavisi et al. | 564/406 |
| 3,155,727 | 11/1964 | Wilson | 564/406 |
| 3,277,175 | 10/1966 | Clemens | 564/406 |
| 3,435,074 | 3/1969 | Terao et al. | 564/406 |

*Primary Examiner*—Paul F. Shaver
*Attorney, Agent, or Firm*—Connolly and Hutz

[57] ABSTRACT

4-nitrodiphenylamines may be produced by an improved process from 4-halo nitrobenzenes and primary aromatic amines in the presence of potassium carbonate and copper compounds, wherein (1) mono- and di-carboxylic acid amides or nitriles are added;
(2) from 3 to 5 mol of amine are introduced per mol of halo nitrobenzene; and
(3) from 1.2 to 2 mol of the amine are added prior to the reaction and the remainder during the reaction so that the molar excess of amine relative to halo nitrobenzene is always from 100 to 400%.

2 Claims, No Drawings

PROCESS FOR THE PRODUCTION OF 4-NITRODIPHENYLAMINES

This application is a continuation of application Ser. No. 862,608, filed 5/12/86, now abandoned.

This invention relates to a process for the production of 4-nitrodiphenylamines by reaction of 4-nitrohalobenzenes with primary aromatic amines in the presence of potassium carbonate and copper compounds.

The reaction of halo nitrobenzenes with aromatic amines has been known for some time. Thus, it is known from DE-PS 185 663 that the reaction may be carried out in the presence of alkali metal carbonates and copper compounds as catalysts.

It is also known that the extremely slow reaction may be accelerated if potassium carbonate is introduced and the water produced by the reaction is removed by azeotropic distillation. According to Example 1 of U.S. Pat. No. 2,927,943, moderately pure 4-nitrodiphenylamine is obtained in an amount of 73% of the theoretical yield in a reaction time of 21 hours under these conditions. It is also known from U.S. Pat. No. 4,155,936 that, during the reaction of halo nitrobenzenes with primary aromatic amines, the disadvantage of long reaction times is accompanied by the contamination of the nitrodiphenylamines by the formation of considerable quantities of tar and by-products, as well as the formation of nitrobenzene by reductive de-halogenation (see U.S. Pat. No. 3,313,854, column 3, lines 64, 65).

In order to overcome these disadvantages, it has been proposed that cocatalysts, solubilizers, as well as dipolar aprotic solvents be added to the reaction mixture.

Formanilide according to U.S. Pat. No. 3,313,854, acetanilide according to DE-AS 1 518 307, salicylanilide according to DE-AS 1 117 594 or ε-caprolactam according to JP 8 122 751 have only a slight effect, however.

The proposals put forward in U.S. Pat. No. 3,121,736 (addition of aminocarboxylic acids, of alkyl diaminopolycarboxylic acids and salts, of disalicylaldiaminoalkanes, of o-hydroxybenzalamino phenols, of polyphosphates, carboxymethylmercapto succinic acid or Schiff bases of salicylaldehydes) in JP-OS 8 240 445 (addition of benzyl trimethylammonium bromide, benzyl tributyl phosphonium chloride, benzyltriphenyl phosphonium chloride, tetramethyl ammonium chloride, tetrabutyl phosphonium chloride), or in DE-OS 3 137 041 (addition of imidazole(ine), pyrimidine, bicyclic amidine, triazine, phenanthroline, dipyridine, bis-quinoline) lead to problems during working-up.

The use of caesium compounds according to DE-OS 3 246 151 produces an improved yield, but the compounds make the process considerably more expensive.

The addition of polyethers of differing structure described in U.S. Pat. No. 4,155,939, JP-OS 80 100 342 and JP-OS 82 02 243 does not produce an improvement either.

Other additions which do not bring about improvements are described in U.S. Pat. No. 3,055,940 (dimethyl formamide and hexamethyl phosphoric acid triamide), U.S. Pat. No. 3,277,175 (dimethyl sulphoxide), DE-OS 2 633 811 (N-methyl pyrrolidone) and JP-OS 71/09452 (diethyl formamide).

A process has now been found for the production of 4-nitrodiphenylamines corresponding to the following general formula (I):

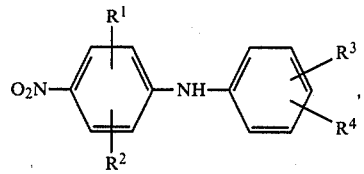

wherein $R^1$, $R^2$, $R^3$ and $R^4$, which may be the same or different, each represents hydrogen or an alkyl radical containing from 1 to 9 carbon atoms; by reaction of halo nitrobenzenes corresponding to the following formula (II):

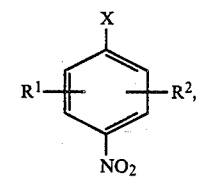

wherein
X represents chlorine or bromine; and
$R^1$ and $R^2$ are as defined above; with primary aromatic amines corresponding to the following general formula (III):

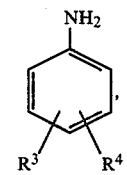

wherein $R^3$ and $R^4$ are defined above; in the presence of potassium carbonate and copper compounds, characterised in that (1) mono- and di-carboxylic acid amides or nitriles are added, (2) from 3 to 5 mole of amine are introduced per mol of halo nitrobenzene and (3) from 1.2 to 2 mole of the amine are added prior to the reaction and the remainder during the reaction in such a way that the molar excess of amine relative to halo nitrobenzene is always from 100 to 400%.

Alkyl radicals $R_1$ to $R_4$ preferably contain from 1 to 3 carbon atoms.

Suitable halo nitrobenzenes include, for example, 4-nitrochlorobenzene, 4-nitrobromobenzene, 4-nitro-2-methylchlorobenzene and 4-nitro-3-methyl-chlorobenzene.

Primary aromatic amines include, for example, aniline, o-toluidine, m-toluidine, p-toluidine, 4-ethylaniline, 4-butylaniline, 4-isopropylaniline, 3,5-dimethylaniline and 2,4-dimethylaniline.

The aromatic amines may obviously also be used in the form of mixtures, in particular mixtures of isomers. From 1 to 6 mol, preferably from 1.5 to 4.5 mol, more preferably from 1.7 to 2.5 mol, of the aromatic amine are generally used per mol of halo nitrobenzene.

The process for the production of 4-nitrodiphenylamine from 4-nitrochlorobenzene and aniline is preferably adopted.

Examples of copper catalysts which may be used in the process according to the present invention include copper-(I)-iodide, copper-(I)-chloride, copper-(II)-chloride, copper-(I)-bromide, copper-(II)-bromide, copper-(I)-cyanide, copper-(I)-oxide, copper-(II)-oxide, copper-(II)-carbonate, basic copper-(II)-carbonate, copper-(II)-sulphate, copper-(II)-nitrate, copper-(II)-formate, copper-(II)-acetate and organic and inorganic coordination compounds of monovalent or divalent copper. It is preferable to use oxygen-containing copper compounds, such as copper-(II)-oxide, copper-(II)-carbonate, basic copper-(II)-carbonate or copper-(I)-oxide, the copper catalyst being used in a quantity of from 0.001 to 0.1, preferably from 0.01 to 0.05, mole per mol of halo nitrobenzene used. The copper catalysts may be used both individually and as mixtures.

Mono- and di-carboxylic acid amides and nitriles include benzamide, 4-methoxy benzamide, acetonitrile, propionitrile, butyronitrile, isobutyronitrile, capronitrile allyl cyanide, methacrylonitrile, benzyl cyanide and malonitrile. Benzamide, propionitrile, isobutyronitrile, methacrylonitrile, benzyl cyanide and malonitrile are preferably used.

The mono- and di-carboxylic acid amides and nitriles are used in a quantity of from 0.01 to 0.1 mol, preferably from 0.025 to 0.05 mol, per mol of halo nitrobenzene.

Rubidium and caesium compounds may also be added to the reaction mixture.

Potassium carbonate may be used in an equivalent quantity or in an excess of up to 1.5 times the equivalent quantity.

The water formed during the reaction is advantageously removed from the reaction mixture by distillation using an entrainer.

Suitable entrainers include, for example, xylene, toluene, benzene, chlorobenzene or chlorotoluene.

The process according to the present invention may be carried out in the presence of additional diluents, for example inert hydrocarbons, such as xylene, if necessary from adjusting or maintaining the reaction temperature range. The aromatic primary amines themselves may also be used for this purpose.

The reaction temperatures for the process according to the present invention may vary widely. They are generally from 140° to 225° C., preferably from 180° to 210° C.

The process according to the present invention may be carried out continuously or batch-wise by conventional methods.

The reaction mixture may also be worked-up in several ways. The salts present in the reaction mixture may be separated by physical means by centrifugation or filtration at elevated temperatures. After washing with hot xylene and drying, a light grey powdery solid remains.

Xylene, unreacted halo nitrobenzene, primary aromatic amine, entrainer and diluent may be completely separated from the filtrate in a rotary evaporator or in a spiral evaporator under a vacuum of from 5 to 50 mbar and at a temperature of from 150° to 220° C., the nitrodiphenylamines being produced as melts which, in turn, solidify on cooling. The mixture obtained as distillate may be introduced into the next charge without further treatment. A further possibility involves partially distilling the filtrate under vacuum and separating most of the nitrodiphenylamines by crystallization. The nitrodiphenylamines are produced in a highly pure form and may thus be further processed directly. The distillate from vacuum distillation and the mother liquor from crystallization may be reused.

In a further embodiment, water is added to the reaction mixture, the potassium salts are dissolved and copper oxide is separated by filtration. Xylene, unreacted p-nitrochlorobenzene and primary amine may be removed from the filtrate by steam distillation. The nitrodiphenylamine is usually produced as a granulate which may be used for further processing.

The copper catalyst may be used several times. To maintain full activity, a quantity of catalyst and cocatalyst which is smaller than that orginally used may optionally be added fresh.

4-nitrodiphenylamines may be produced in high yields and at high purity in short reaction times by the process according to the present invention. By-products are only formed to a slight extent during the process according to the present invention.

The 4-nitrodiphenylamines produced by the process according to the present invention may easily be reduced to aminodiphenylamines by known processes and, as such, are valuable intermediates for the production, for example, of dyes or stabilizers for rubber (see U.S. Pat. No. 3,163,616).

EXAMPLE 1

157.6 g of p-nitrochlorobenzene, 186 g of aniline, 100 g of potassium carbonate, 20 ml of xylene, 2 g of copper oxide and 3 g of benzamide were placed in a 1 l flask with stirrer and distillation attachment with water separator.

The reaction mixture was heated to 195° C. with stirring. A further 186 g of aniline in total was then added portion-wise and the contents of the flask were maintained at a temperature of 195° C. until from 10.5 to 11 ml of water had separated and the 4-chloro-nitrobenzene content of a sample was determined by liquid chromatography. If the 4-chloronitrobenzene content was below 1.5% of the original quantity, the reaction was interrupted by cooling otherwise continued again until this value was reached. The total duration of the reaction was 12 hours.

The reaction mixture was treated with 250 ml of water, filtered at 90° C. and the volatile fractions were then removed using steam. The aqueous phase of the flask contents was separated, and the organic phase solidified on cooling. 212.8 g of a yellow granular substance was obtained which, according to analysis by liquid chromotography, contained 88.0%, by weight, of 4-nitrodiphenylamine, corresponding to an 88.3% yield, based on 4-nitrochlorobenzene.

Further experiments produced the following results:

| Example | Addition | Quantity of Addition (g) | Reaction Time (h) | 4-nitrodiphenyl-amine content (%, by weight) | Yield of crude 4-nitrodiphenyl amine (g) | Yield (% of th.) |
|---|---|---|---|---|---|---|
| 2 | Propionitrile | 5.51 | 10.0 | 89.2 | 212.4 | 88.4 |
| 3 | Isobutyronitrile | 6.91 | 9.0 | 91.9 | 214.6 | 91.9 |
| 4 | Capronitrile | 2.43 | 11.0 | 89.3 | 212.8 | 88.7 |
| 5 | Methacrylonitrile | 1.68 | 10.0 | 88.1 | 212.6 | 87.5 |
| 6 | Benzyl cyanide | 2.93 | 12.5 | 89.1 | 214.2 | 89.1 |

| Example | Addition | Quantity of Addition (g) | Reaction Time (h) | 4-nitrodiphenyl-amine content (%, by weight) | Yield of crude 4-nitrodiphenyl amine (g) | Yield (% of th.) |
|---|---|---|---|---|---|---|
| 7 | Malonitrile | 2.67 | 8.0 | 90.7 | 213.2 | 90.4 |

We claim:

1. A process for the production of 4-nitrodiphenylamines corresponding to the following general formula

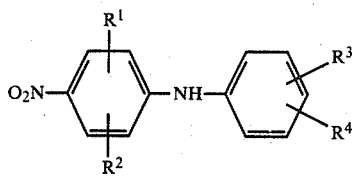

wherein
$R^1$, $R^2$, $R^3$ and $R^4$, which may be the same or different, represent hydrogen or an alkyl radical containing from 1 to 9 carbon atoms;
by reaction of halo nitro compounds corresponding to the following general formula:

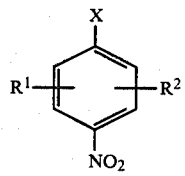

wherein
X represents chlorine or bromine, and
$R^1$ and $R^2$ are as defined above; with primary aromatic amines corresponding to the following general formula:

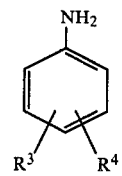

wherein
$R^3$ and $R^4$ are as defined above; in the presense of potassium carbonate and copper compounds, characterised in that (A) benzamide, 4-methoxy benzamide, acetonitrile, propionitrile, butyronitrile, isobutyronitrile, capronitrile, allyl cyanide, methacrylonitrile, benzyl cyanide or malonitrile are added in an amount of 0.01 to 0.1 mol per mol of halo nitrobenzene, (B) from 1 to 6 mol of amine are introduced per mol of halo nitrobenzene and (C) from 1.2 to 2 mol of the amine are added prior to the reaction in such a way that the molar excess of amine relative to halo nitrobenzene is always from 100 to 400%.

2. A process according to claim 1, characterised in that $R_1$, $R_2$, $R_3$ and $R_4$ represent hydrogen.

* * * * *